(12) United States Patent
Chow et al.

(10) Patent No.: US 7,025,789 B2
(45) Date of Patent: Apr. 11, 2006

(54) PROSTHETIC DEVICE AND METHOD FOR TOTAL JOINT REPLACEMENT IN SMALL JOINT ARTHROPLASTY

(75) Inventors: Shew Ping Chow, Hong Kong (CN); Kwok Wai Lam, Hong Kong (CN); Ian Gibson, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 10/425,465

(22) Filed: Apr. 29, 2003

(65) Prior Publication Data
US 2004/0220678 A1    Nov. 4, 2004

(51) Int. Cl.
*A61F 2/42* (2006.01)

(52) U.S. Cl. .................................................. 623/21.11
(58) Field of Classification Search ............. 623/21.11, 623/21.15, 21.19, 20.11–20.15, 20.21, 21.13, 623/21.16
See application file for complete search history.

(56) References Cited

U.S. PATENT DOCUMENTS

| | | | | |
|---|---|---|---|---|
| 4,242,759 A | * | 1/1981 | White | 623/21.15 |
| 4,568,348 A | * | 2/1986 | Johnson et al. | 623/20.29 |
| 4,642,122 A | * | 2/1987 | Steffee | 623/21.19 |
| 5,047,059 A | * | 9/1991 | Saffar | 623/21.15 |
| 5,776,201 A | * | 7/1998 | Colleran et al. | 623/20.15 |
| 6,485,519 B1 | * | 11/2002 | Meyers et al. | 623/20.24 |
| 6,689,169 B1 | * | 2/2004 | Harris | 623/21.16 |
| 2003/0163201 A1 | * | 8/2003 | McMinn | 623/20.29 |

* cited by examiner

Primary Examiner—Pedro Philogene
(74) Attorney, Agent, or Firm—Dickstein, Shapiro, Morin & Oshinsky, LLP.

(57) ABSTRACT

The prosthesis device can have a pair of articular members adapted to be mounted onto adjoining bones, respectively, to replace a joint. The first and second articular members can have first and second bearing elements, respectively. The bearing elements can be formed to be capable of replacing at least a portion of the bone ends of the adjoining bones, respectively, and providing an articulation close to that of a natural joint. The bearing elements can be fixed to the respective bones through an initial implant fixation achieved by press-fit anchoring immediately after surgery and/or a secondary implant fixation established from bone-ingrowth.

41 Claims, 8 Drawing Sheets

PROSTHETIC DEVICE AND METHOD FOR TOTAL JOINT REPLACEMENT IN SMALL JOINT ARTHROPLASTY

FIELD OF INVENTION

The present invention relates generally to a prosthetic device. In particular, the invention relates to a prosthetic joint replacement for reconstructing the articulation such as those in finger joint or other comparable synovial joints. The invention also relates to a method of using a surgically implantable prosthetic device which substantially resembles the original anatomical structure of the joint.

BACKGROUND OF THE INVENTION

While muscle pull on flexor or extensor provides a turning moment to facilitate joint motion, the stability of a joint in either a still position or motion depends on both the constraints of the natural bicondylar joint structure and the integrity of the soft tissue mechanisms. Typical joint motions include restricted flexion and rotational and lateral deviation by constraints from the bicondylar joint configuration and ligamentous support. For example, the normal motion range of a proximal interphalangeal (PIP) joint is around 0° in extension to 100° in full flexion with restricted rotational and lateral deviation. The motion of a PIP joint is similar to that of a single axis hinge joint, in which the rotation axis is parallel to an articulating surface allowing the joint to flex in a uniplanar motion. Mobility of finger joints especially in metacarpophalangeal (MCP) and PIP joints is critical for providing normal grasp and pinch for various hand functions in daily activities.

Injuries such as bone fracture or joint damage can lead to loss of joint function, pathological disturbance by osteoarthritis, posttraumatic arthritis and rheumatoid arthritis. Affected joints usually end up with erosions in the articular cartilage and bone resulting in unstable bony support, synovitis and inflammatory responses, which can destroy surrounding soft tissue. Consequences from progressive joint destruction are pain, joint instability, loss of mobility, excessive deformity and unrecoverable disability of hand function from soft tissue rupture.

Surgical intervention by implanting arthroplasty has been implemented to restore destroyed or deformed articulations to thus relieve pain, restore joint motion, correct deformity, and improve motion function prior to any salvage procedure of arthrodesis or removal of the joint. Artificial joint prostheses have been used in large joint replacement. However, small joint arthroplasty in particular finger joint replacement has not achieved the same results. The inability to reproduce the complex anatomical structure of the joint and the small size of joint components presents long-term clinical problems and renders surgical procedures difficult.

U.S. Pat. No. 3,466,669 discloses a fully constrained hinge type prosthesis, which can restore some joint function, in particular relieve pain. However, such fully constrained hinge type prosthesis cannot restore the normal arc of rotation. Consequently, excessive stress can exert on the bone implant interface resulting in progressive bone resorption with consequent prosthetic loosening and bone penetration.

U.S. Pat. Nos. 3,462,765 and 5,824,095 disclose one piece hinge type designs, using flexible silicon material. But there are concerns in the long-term performance of these implants since they can restore only a limited range of motion of around 30–40 degrees in flexion. In addition, both silicon breakages and silicon-induced synovitis from silicon wear particles are frequently reported.

The problems arising from constrained implants were dealt with by finger joint prostheses with semi-constrained articulation, such as designs from RMS and DJOA, increase the post-operative range of motion. In such designs, the articulating surfaces are modeled to closely resemble the anatomical shape of a real joint with no linking inbetween. The joint stability thus relies mostly on the integrity of the surrounding soft tissue, such as the collateral ligament and the volar plate. However, due to muscular imbalance, a potential recurrence of joint deformity still exists. Moreover, aseptic loosening stimulated by induced particles originated from polyethylene components is still unsolved in joint arthroplasty.

The present invention provides a prosthetic device that is capable of reducing complications and deficiencies arising from previous finger joint prostheses. For example, the prosthetic device of the invention is capable of providing efficient pain relief, increased movement range, enhanced fixation, intrinsic joint stability, and extended durability. The invention also provides an improved surgical technique by using a surgically implantable device which substantially resembles the original anatomical structure of a finger joint so that other surgical reconstructions to the adjacent soft tissue structures can be carried out at the same time.

SUMMARY OF THE INVENTION

The present invention relates generally to a prosthesis device, such as a joint prosthesis capable of closely functioning as a natural joint. The prosthesis device can comprise a pair of articular members adapted to be mounted onto adjoining bones, respectively. The articular members can comprise bearing elements, respectively, which are capable of providing an articulation closely to that of a natural joint. The prosthesis device so formed is capable of providing the mobility and the stability close to that of a natural joint. Additionally or alternatively, the prosthesis device is capable of affording the least alteration to the surrounding tendon mechanism and ligamentous support followed by surgical intervention.

In particular, the invention relates to a finger joint prosthesis for resurfacing an articulation at the site of the proximal interphalangeal (PIP) joint. The joint prosthesis can comprise two articular members. Each of the articular members can comprise an artificial bearing element with cylindrical configuration functionally substituting the role of articular cartilage to achieve a range of motion near normal. One preferred embodiment for the invention is a combined fixation system followed firstly by a conformed seating between backing facets beneath each bearing element and prepared bone ends, and secondarily by a double-stage intramedullary fixation stem which together can stably locate each articular member onto respective phalangeal bone with enhanced bone-implant integrity for effective distribution of load components to bony support.

According to another aspect of the present invention, an improved surgical method is provided for joint reconstruction by adapting the anatomical structure of a natural finger joint for the implant design. Bearing elements in trapezoidal and elliptical outer profiles according to an anatomical structure are implanted to resurface portions of destroyed articular cartilage. Surgical resection based on a disclosed anatomical structure retains maximal bone stock at each phalangeal bone end, in particular bypassing every attachment of collateral ligaments, central extensor tendon and the volar plate which are deemed to be critical for adequate joint stability. The surgical method according to the invention allows each functional soft-tissue mechanism surrounding the location of joint replacement to be preserved substantially for maintaining muscular balance as a normal joint.

Common joint problems secondary to disability of hand function are joint deformity and dislocation arising from imbalanced tendon load and loosened ligamentous supports of a destroyed articulating joint. Another advantageous embodiment currently presented to deal with these problems is its intrinsic joint stability as constituted by semi-constrained features which are defined as cylindrically configured bearing couple, circumferential guiding pair, dorsal end run and dorsal protruded edge on the respective articular members. Based on these semi-constrained features, a diseased joint subsequent to implantation is allowed to reproduce not only a normal range of motion with counterbalanced joint stability, but also any abnormal joint activities such as lateral pivoting motion, dorsal subluxation as well as swan-neck deformity could be suppressed accordingly.

With all distinctive features successfully introduced by the preferred embodiments of the present invention and applied in finger joint arthroplasty, a unique solution deals with shortcomings and complications arising from the state of the art is introduced. Other proposing considerations and advantageous aspects according to the present invention are readily apparent in the following detail description in conjunction with corresponding illustrations where the scope of the invention is set out in the appended claims.

BRIEF DESCRIPTION OF THE DRAWINGS

The detailed description of the present invention will be better understood in conjunction with the accompanying drawings, wherein like reference characters represent like elements, as follows.

DETAILED DESCRIPTION OF THE INVENTION

Exemplary prosthesis devices embodying the principles of the present invention are shown throughout the drawings. In the following description of various embodiments of prosthesis devices, similar elements or components thereof are designated with the same reference numbers and redundant description is omitted.

Figure 2:
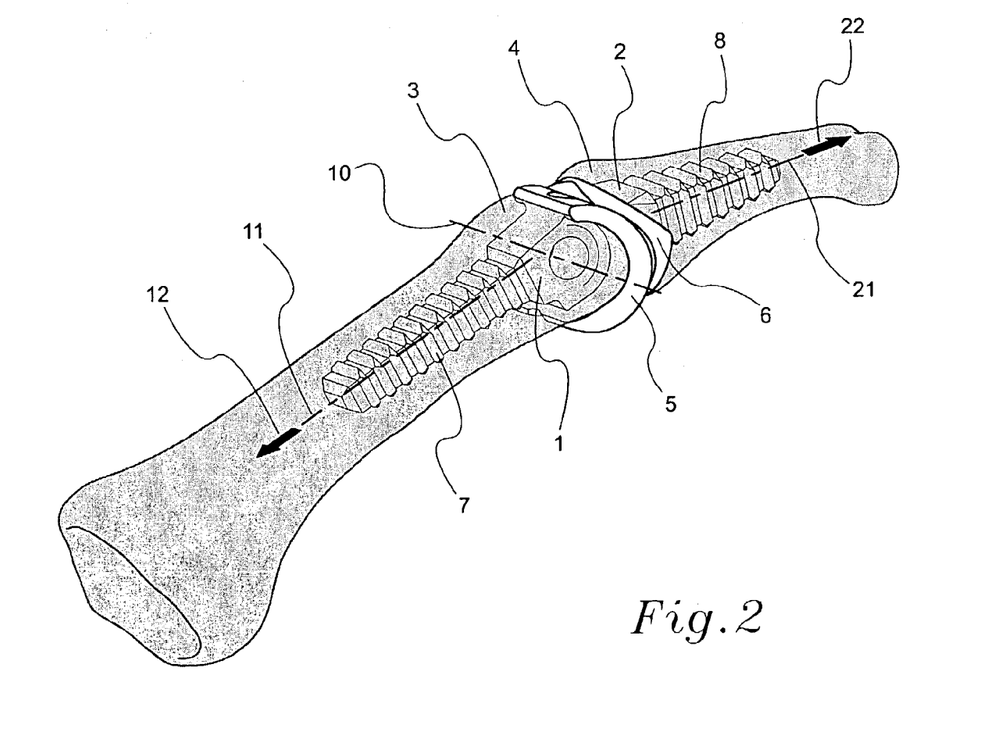
FIG. 2 is a perspective view of an exemplary prosthetic device after being implanted in adjoining bones.

The prosthesis device can comprise a pair of articular members 1 and 2 adapted to be mounted onto adjoining bones 3 and 4, respectively, to replace a joint. The first and second articular members 1 and 2 can comprise first and second bearing elements 5 and 6, respectively. The bearing elements 5 and 6 can be formed to be capable of replacing at least a portion of the bone ends of the adjoining bones 3 and 4, respectively, and providing an articulation close to that of a natural joint, as will be described in detail below. The bearing elements 5 and 6 can be fixed to the respective bones 3 and 4 through an initial implant fixation achieved by press-fit anchoring immediately after surgery and/or a secondary implant fixation established from bone-ingrowth. In one embodiment, the bearing elements 5 and 6 can be implanted into and mounted onto adjoining bones 3 and 4 through stem elements 7 and 8, respectively. In an exemplary embodiment, such as shown in FIG. 2, the first stem element 7 can be formed extending from the first bearing element 5 and along a first longitudinal axis 11 towards the free end of the stem element 7 in the direction of a first proximal insertion 12. In another exemplary embodiment, such as shown in FIG. 2, a second stem element 8 can be formed extending from the second bearing element 6 and along a second longitudinal axis 21 towards the free end of the stem element 8 in the direction of a second proximal insertion 22.

The prosthesis device so formed is capable of replacing a joint and closely functioning as a natural joint and providing the mobility and the stability close to that of a natural joint. For example, the prosthesis device is capable of substantially carrying out the basic flexion and extension of a natural joint and thus functioning as an alternative articulation of a natural joint. In an exemplary embodiment, the coupled bearing elements 5 and 6 are capable of providing a uniaxial joint motion, such as for an implanted bone end to slide freely over the adjoining bone end along a common joint rational axis 10, such as shown in FIG. 2. Additionally or alternatively, the prosthesis device is capable of affording the least alteration to the surrounding tendon mechanism and ligamentous support followed by surgical intervention.

Figure 1:
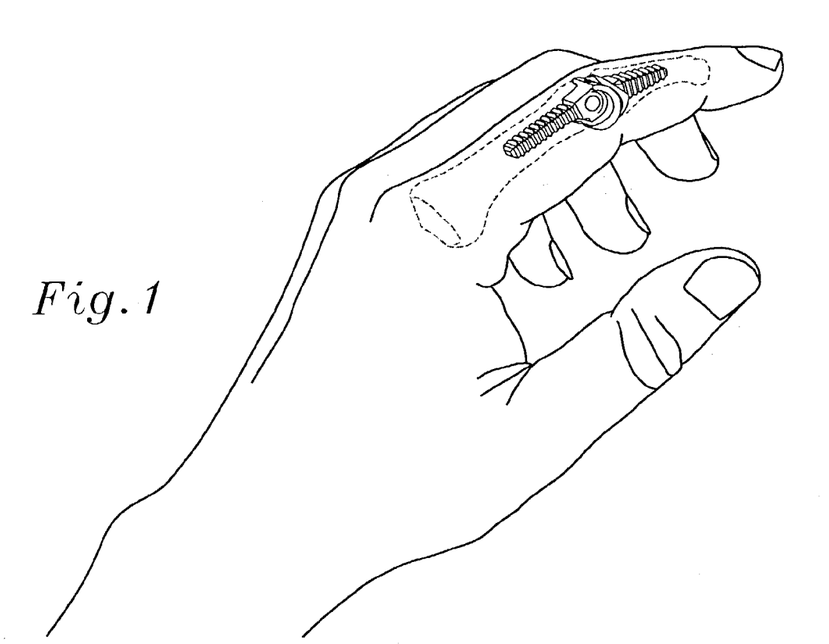
FIG. 1 illustrates an exemplary prosthetic device implanted in the phalangeal bones of the left index finger.
Figure 3A:
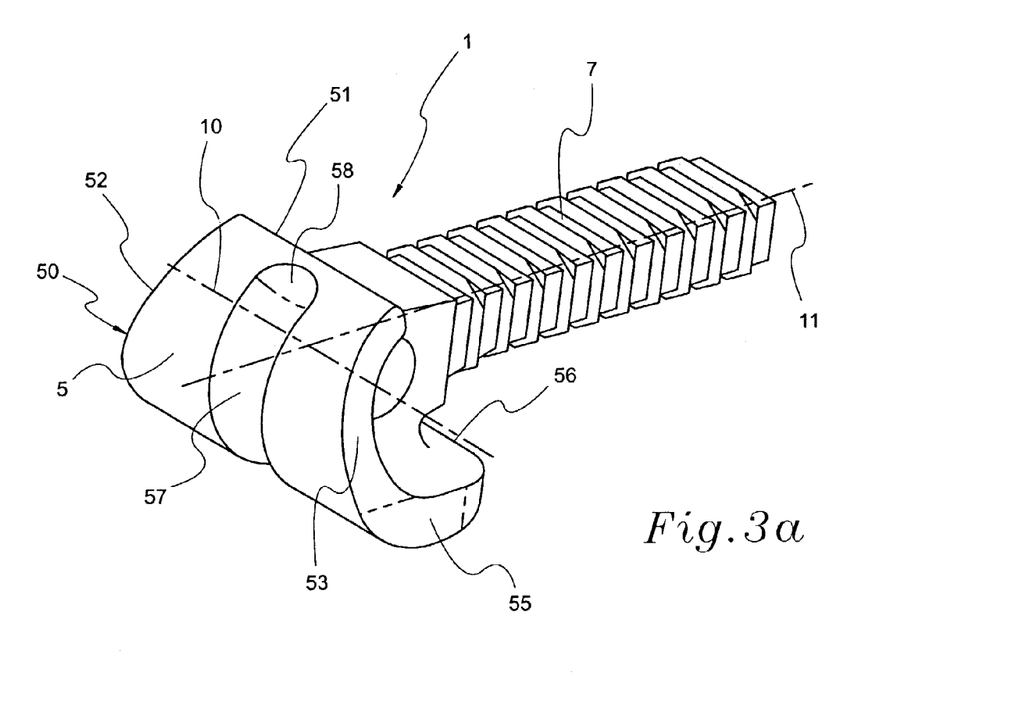
FIG. 3a is a perspective view of the first articular member as in FIG. 2 showing the convex bearing element.
Figure 3B:
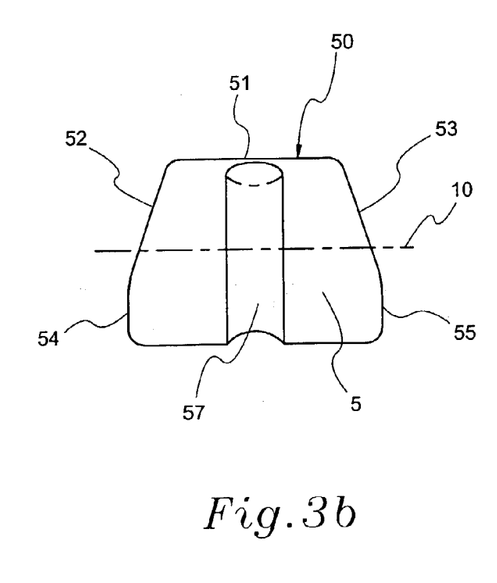
FIGS. 3b and 3c are different end views of the first articular member showing the profiles of its bearing element.
Figure 3C:
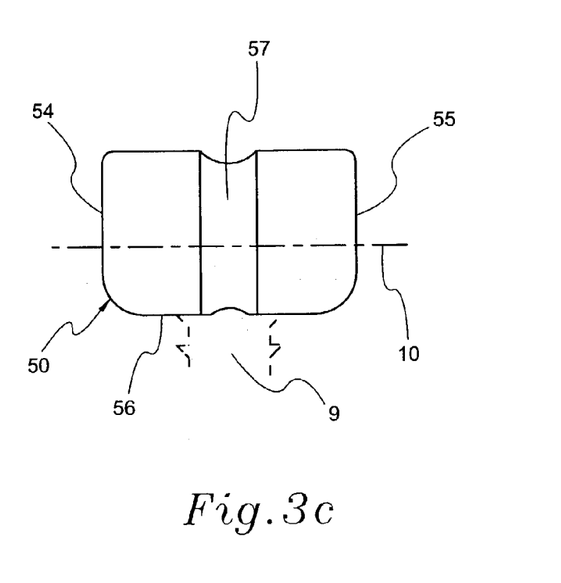

In one embodiment, such as shown in FIG. 1, the prosthesis device can be formed as a finger joint prosthesis. In an exemplary embodiment, the articular members 1 and 2 can be adapted to be implanted in or otherwise mounted onto the adjoining phalangeal bones, such as the phalangeal bones of a left index finger as shown in FIG. 1. Each bearing element 5 or 6 can be adapted to replace at least a portion of the bone end of a phalangeal bone after being implanted therein or otherwise mounted thereonto. In an exemplary embodiment, the bearing elements 5 and 6 can be formed to be capable of coupling with each other in a congruent engagement. For example, the bearing elements 5 and 6 can comprise the trapezoidal and elliptical shapes complementary to the natural bone ends, such as the head of proximal phalanx 3 and the base of middle phalanx 4, respectively. Although the prosthesis device in this embodiment is shown as a finger joint prosthesis used at the proximal interphalangeal site, it should be understood that the prosthesis device can be used to replace other joints as well. Detailed description of the articular members 1 and 2, as being used in all types of prosthesis devices, is provided as follows:

The first articular member 1 of the prosthetic device can be in various forms and adapted to at least partially replace a portion of a bone, such as bone 3. In one exemplary embodiment, such as shown in FIGS. 3a to 3c, the first bearing element 5 of the first articular member 1 can be formed to at least partially replace a bone end. In an exemplary embodiment, the first bearing element 5 can comprise a first bearing surface 50 formed in various shapes for resurfacing the articulating surface at a bone end, such as the head of a proximal phalanx 3. For example, the first bearing surface 50 can comprise a generally curved surface. In one exemplary embodiment, the first bearing surface 50 can comprise a substantially convex surface. In another exemplary embodiment, the first bearing surface 50 can be a portion of a cylindrical surface.

Additionally or alternatively, the first bearing element 5 can be formed to be capable of articulating with a corresponding bone end, or a replaced bone end such as the second bearing element 6, to carry out the articulation of the resurfaced joint. In an exemplary embodiment, the first bearing surface 50 can be formed to be capable of movably engaging with an adjoining bone end surface or a resurfaced bone end, such as the second bearing surface 60. In another exemplary embodiment, at least a portion of the first bearing surface 50 can be formed to be complement to a portion of the second bearing surface 60, such as to allow the bearing elements 5 and 6 to articulate and carry out the basic flexion and extension of a natural joint.

In one embodiment, the first bearing surface 50 can be formed by a top edge 51, a bottom edge 56, and two side edges 54 and 55. In an exemplary embodiment, the top edge 51 can be adapted to be positioned in conjunction with the dorsal cortex at a bone end, such as the head of proximal phalanx 3. In another exemplary embodiment, the bottom edge 56 can be substantially parallel to the top edge 51. In a further exemplary embodiment, the side edges 54 and 55 can extend substantially perpendicularly to the bottom edge 56. In one exemplary embodiment, the bearing surface 50 can comprise side edges 54 and 55 that can be tapered towards the top edge 51, such as shown in FIG. 3b. In an exemplary embodiment, the tapered edges 52 and 53 can be symmetrically positioned and smoothly merged with the side edges 54 and 55, respectively.

In one exemplary embodiment, such as shown in FIG. 3b, the first bearing surface 50 can have a substantially trapezoidal shape when viewing in the direction of the first proximal insertion 12. In such a substantially trapezoidal bearing surface 50, the decreasing joint contact area towards the top edge 51 is capable of providing a less congruent bearing couple, which can provide a certain degree of joint flexibility to a mating surface while the adjoining bones are in a state of extension. Additionally or alternatively, the bearing surface 50 can have a fairly constant width of joint contact area, such as shown in FIG. 3c, when viewing from the side of the bottom edge 56 and in a direction perpendicular to the first longitudinal axis 11. The increasing contact area at bottom region is capable of enhancing the joint stability and support to the adjoining a second bearing element 6 to maximize the allowable area for distributing contact stresses over the bearing element 5 when the joint is in a necessary flexion angle, such as for a power gripping function by the finger. It will be appreciated that various other embodiments of the first bearing element 5 and the first bearing surface 50 for similar functions are also within the scope of the present invention.

Figure 4A:
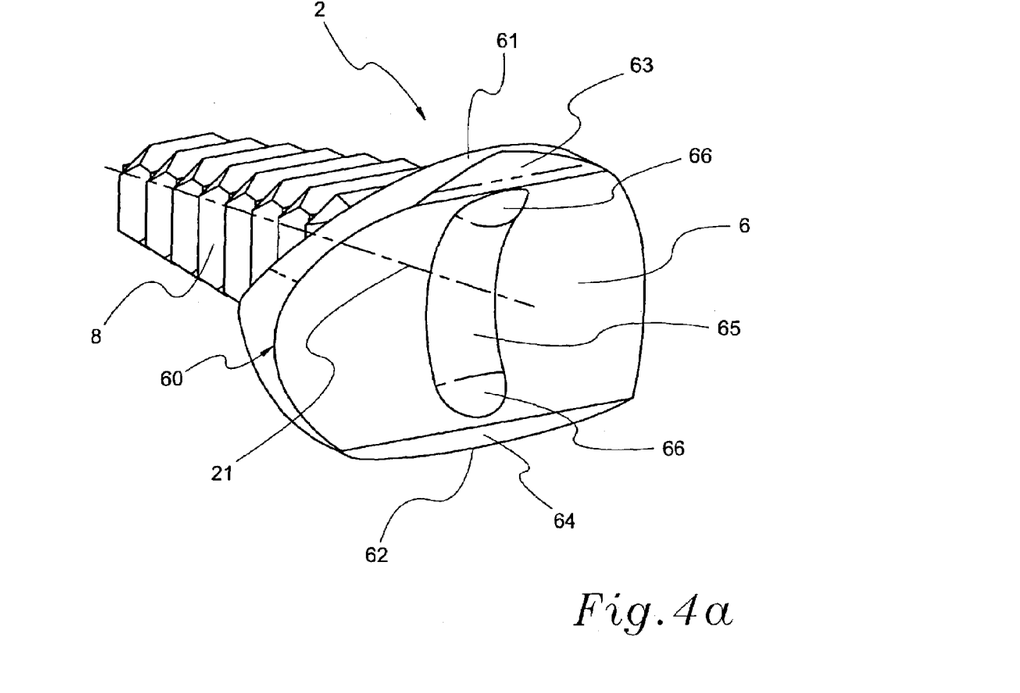
FIG. 4a is a perspective view of the second articular member as in FIG. 2 showing the concave bearing element.
Figure 4B:
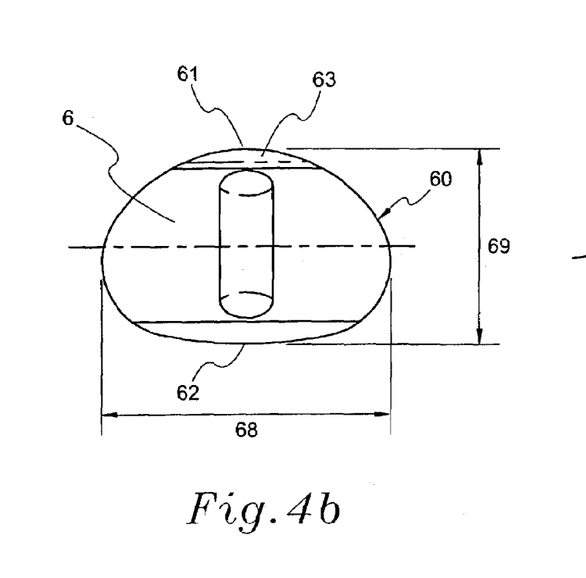
FIGS. 4b and 4c are end view and partial side view, respectively, of the second articular member showing the profiles of its bearing element.
Figure 4C:
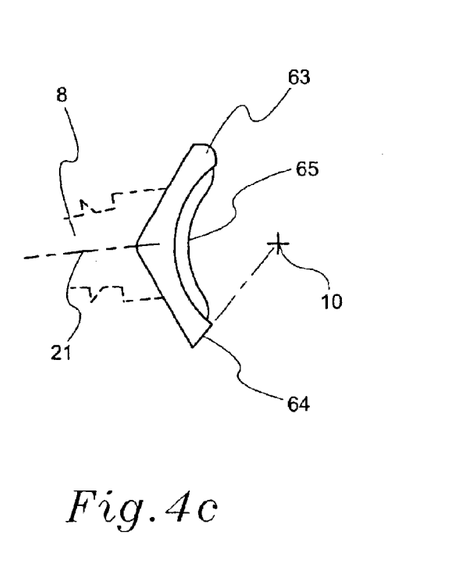

The second articular member 2 of the prosthetic device can be in various forms and adapted to at least partially replace a portion of a bone, such as bone 4. In one exemplary embodiment, such as shown in FIGS. 4a to 4c, the second bearing element 6 of the second articular member 2 can be formed to at least partially replace a bone end. In an exemplary embodiment, such as shown in FIGS. 4a to 4c, the second articular member 2 can comprise a second bearing surface 60 formed in various shapes and adapted to resurface a bone end. For example, the second bearing surface 60 can comprise a generally curved surface. In one exemplary embodiment, the bearing surface 60 can comprise a substantially concave surface adapted to resurface an articulating surface of a bone end, such as the base of a middle phalanx 4. In another exemplary embodiment, the bearing surface 60 can be a portion of a cylindrical surface.

Figure 5A:
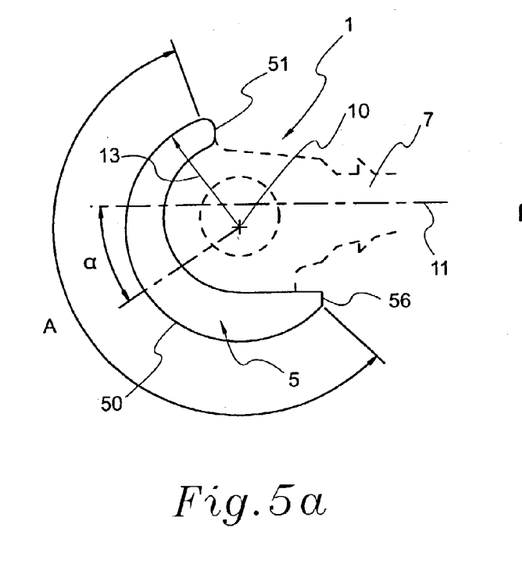
FIGS. 5a and 5b are partial side views of the first and second articular members, respectively.

Additionally or alternatively, the second bearing element 6 can be adapted to articulate with an adjoining bone end, or a corresponding replaced bone end, such as the first bearing element 5, and carry out the articulation of a natural joint. In an exemplary embodiment, the second bearing surface 60 can be adapted to movably engage with an adjoining bone end or a resurfaced bone end, such as the first bearing surface 50 as shown in FIG. 5c. For example, at least a portion of the second bearing surface 60 can be formed to be complement to a portion of the first bearing surface 50, such as to allow the bearing elements 5 and 6 to articulate with each other and carry out the basic flexion and extension of a natural joint. In an exemplary embodiment, the second bearing surface 60 can be a concave surface complementary to a convex first bearing surface 50.

In one exemplary embodiment, such as shown in FIGS. 4a and 4b, the second bearing surface 60 can comprise a substantially elliptical shape having a major diameter 68 and a minor diameter 69. In an exemplary embodiment, the ratio of the major diameter 68 to the minor diameter 69 can range from about 1.3 to about 1.6. In another exemplary embodiment, the bearing surface 60 can comprise two halves of elliptical arc portions 61 and 62. In an exemplary embodiment, the two arc portions 61 and 62 can have different radii of curvature, such as shown in FIG. 4b. In another exemplary embodiment, the radius of the volar arc portion 62 can be in a scale factor from about 2.5 to about 2.9 larger than the radius of the dorsal arc portion 61. It will be shown appreciated that various other embodiments of the second bearing surface 60 are also within the scope of the present invention.

In one embodiment, the second bearing element 6 can be adapted to minimize the interference with the surrounding soft tissue. Thus, any high joint load arising from the regular joint function can be partially distributed to the surrounding soft tissue mechanisms to reduce the reaction load imposed between the joint interface, such as bearing surfaces 50 and 60. As a result, the prosthesis device can effectively remodel a joint balance from problematic bone and ligamentous deficiencies, which can be critical in assisting joint reconstruction to reproduce functional stability of an affected joint. In one exemplary embodiment, the second bearing element 6 can comprise a dorsal protruding lip 63 formed between the second bearing surface 60 and the dorsal arc portion 61, such as shown in FIGS. 4a to 4c. In an exemplary embodiment, the dorsal protruding lip 63 can be formed to be capable of compensating for possible eroded bony support at the dorsal extremity on the base of the bone 4 to resist potential dorsal subluxation between the articular members 1 and 2. For example, the dorsal protruding lip 63 is capable of pushing the surrounding extensor tendon slightly away from the contact gap between the matching bearing elements 5 and 6 to thereby protect the extensor mechanism from potential erosion and damage to the soft tissue structure. In an exemplary embodiment, the dorsal protruding lip 63 can be a substantially round edge protruding outwardly from the second bearing element 6, such as shown in FIG. 4c.

In another exemplary embodiment, the second bearing element 6 can comprise a volar recessed facet 64 formed between the bearing surface 60 and the volar arc portion 62, such as shown in FIGS. 4a to 4c. In an exemplary embodiment, the volar recessed facet 64 can be a flat cut-out surface orientated towards the joint rotational axis 10, such as in FIG. 4c. The volar recessed facet 64 can be adapted to accommodate natural arrangements of the extensor tendon and volar plate respectively and reduce the interference to the surrounding soft tissue. It will be shown appreciated that various other embodiments of the bearing element 6 are also within the scope of the present invention.

In one embodiment, the bearing elements 5 and 6 can be formed to provide various articulating ranges. In an exemplary embodiment, such as shown in FIG. 5a, the first bearing element 5 can have an arc bearing surface 50 expanding for various arc ranges A. For example, the first bearing surface 50 can have an arc expansion of more than 180 degrees. In a preferred embodiment, the arc bearing surface 50 can expand for about 200 degrees. In another exemplary embodiment, such as shown in FIG. 5a, the arc bearing surface 50 can be angularly and palmarly displaced for an angle a from the first stem axis 11. Such a displacement of the arc bearing surface 50 can provide an extended articulating surface towards the volar side of the bearing element 5 for adequate support at joint flexion. In one exemplary embodiment, the arc bearing surface 50 can be about 30 degrees displaced angularly and palmarly from the first stem axis 11.

Figure 5B:
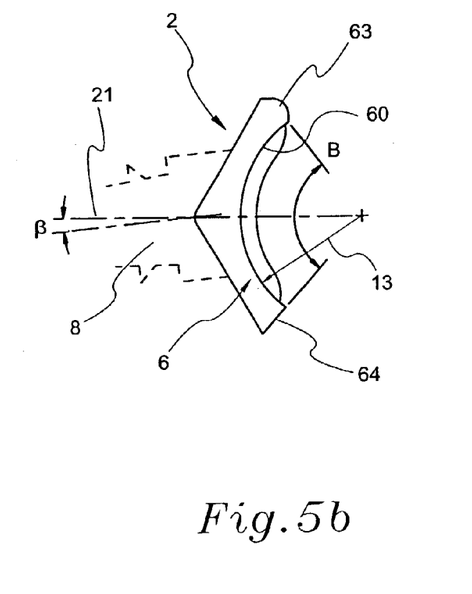
Figure 5C:
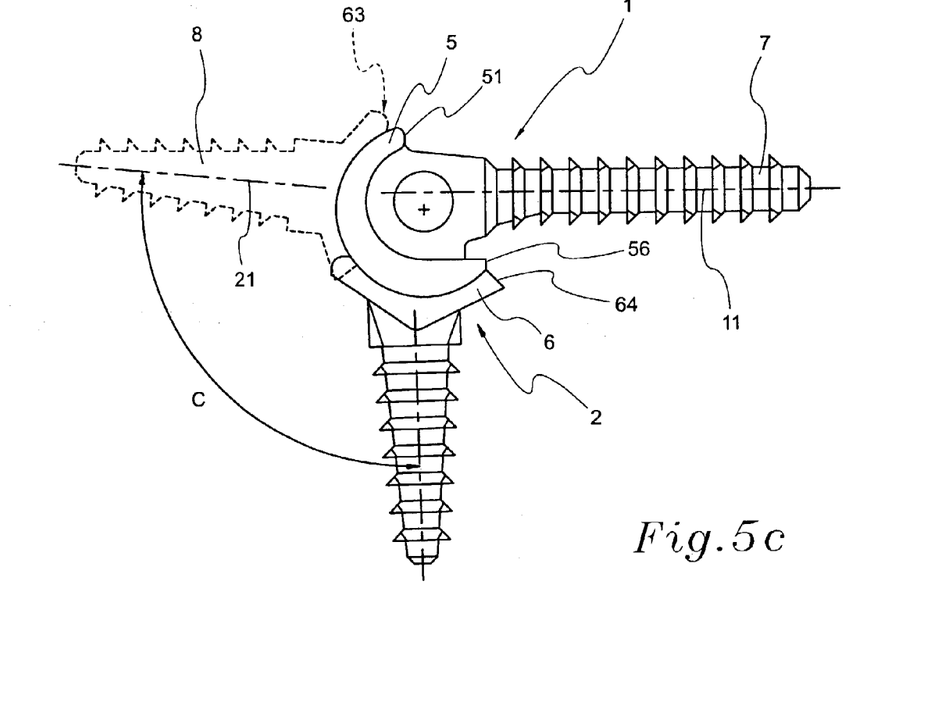
FIG. 5c shows a sliding contact of the two articular members and the rotational movement range of the second articular member with respect to the first articular member.

In another exemplary embodiment, such as shown in FIG. 5b, the second bearing element 6 can have an arc bearing surface 60 expanding for various arc ranges B. For example, the second bearing surface 60 can have an arc expansion for about 90 degrees. In one exemplary embodiment, the arc expansion can be angularly and dorsally displaced for an angle β from the second stem axis 21. For example, the displacement angle β can be from 5 degrees to about 10 degrees. In an exemplary embodiment, the arc bearing surface 60 can be about 6 degrees displaced angularly and dorsally from the second stem axis 21, such as shown in FIG. 5b.

In another embodiment, the bearing elements 5 and 6 can be adapted to movably engage with each other to carry out the articulation, such as of a natural joint. For example, the bearing surfaces 50 and 60 can be in a sliding contact with each other, such as shown in FIG. 5c. In one exemplary embodiment, the bearing surfaces 50 and 60 can be formed as complementary cylindrical surfaces with the same joint radius 13. In an exemplary embodiment, the bearing elements 5 and 6 are capable of engaging with each other at a dorsal position where the dorsal edge 51 meet with the dorsal protruding lip 63, such as shown by the dashed line engagement in FIG. 5c. In another exemplary embodiment, the bearing elements 5 and 6 are capable of engaging with each other at a palmar position where the volar edge 56 meets with the volar recessed facet 64, such as shown by the solid line engagement in FIG. 5c. In a further embodiment, the bearing elements 5 and 6 can be formed to be capable of articulating in various ranges, such as close to that of the natural articular cartilage. In an exemplary embodiment, such as shown in FIG. 5c, the bearing element 6 of the second articular member 2 is capable of moving between a dorsal position and a palmar position around the joint rotational axis 10. In another exemplary embodiment, the motion range of the prosthetic device can reproduce a flexion arc range of about 100 degrees, which is comparable to the normal functional range of a PIP joint.

In addition to the provision of an articulation of a natural joint, the prosthetic device can also be formed in various manners to provide an adequate joint stability, such as to remedy any inferior soft tissue integrity such as resulting from degenerative diseases or rheumatoid arthritis, or otherwise increase the intrinsic joint stability. For example, the prosthetic device can be made semi-constrained, such as by the structures of the bearing elements 5 and 6.

In one embodiment, the prosthetic device can be formed to limit angulations between the bearing elements 5 and 6. In an exemplary embodiment, the bearing surfaces 50 and 60 can be cylindrically shaped and be coupled with each other around the joint rotation axis 10. Such cylindrical configuration of the bearing elements 5 and 6 is capable of eliminating angulations, which can be possible from a circular condylar configuration. In addition, the coupled cylindrical bearing elements 5 and 6 can have a straight supporting contact edge, which can extend parallel to the joint rotation axis 10, such as apparent in sectional view FIG. 6. In such an exemplary embodiment, any contact stresses can be evenly dispersed along the longitudinal direction of the bearing elements 5 and 6 to thus minimize the wear and tear and extend the service life of the prosthetic device.

Figure 6:
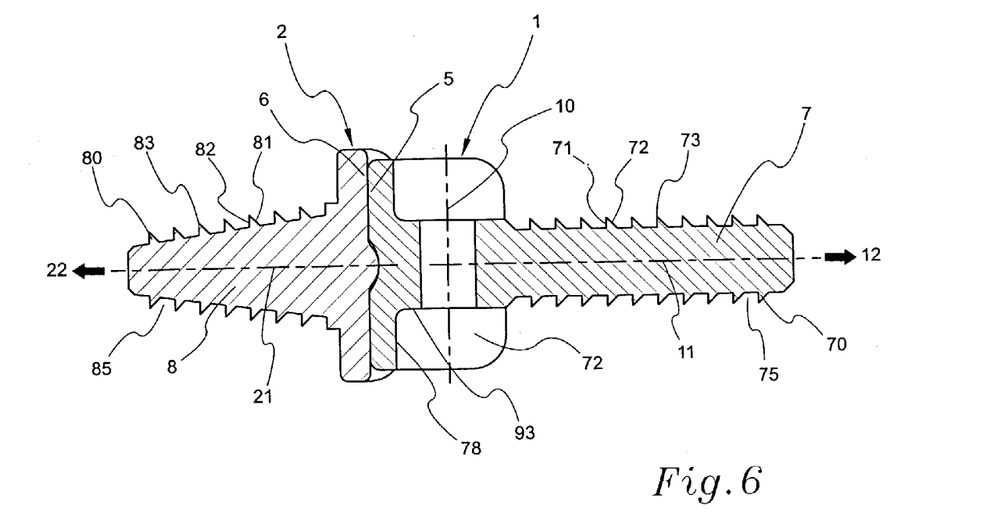
FIG. 6 is a top sectional view of the first and second articular members showing the contact between the respective bearing elements thereof.

In another embodiment, the prosthetic device can be formed to be capable of providing lateral alignment and constraint to the articular members 1 and 2 and/or counteracting laterally imposed load and imbalanced ligamentous supports of an affected joint to thus increase the joint stability. For example, one of the bearing elements 5 and 6 can comprise a guiding track 57, such as shown in FIGS. 3a to 3c, while the other of the bearing elements 5 and 6 can comprise a guiding ridge 65, such as shown in FIGS. 4a to 4c. In an exemplary embodiment, the guiding track 57 and the guiding ridge 65 can couple with each other to provide an alignment of the bearing elements 5 and 6. In another exemplary amendment, the guiding track 57 can be adapted to receive the guiding ridge 65 to thereby resist undesired lateral movement of the bearing elements 5 and 6. For example, the guiding track 57 and the guiding ridge 65 can have complementary circular shapes, such as shown in FIG. 6. In an exemplary embodiment, such as shown in FIGS. 3a to 3c, a guiding track 57 can be provided to extend circumferentially on the first bearing surface 50 for receiving a guiding ridge 65 formed on the second bearing surface 60. In another exemplary embodiment, the guiding ridge 65 can extends circumferentially on the bearing surface 60, such as shown in FIGS. 4a to 4c.

In an exemplary embodiment, the guiding ridge 65 can be formed to be capable of running freely along the guiding track 57 while the prosthetic device is in motion and continuing to provide lateral alignment and constraint to the bearing elements 5 and 6. In another exemplary embodiment, the guiding track 57 and the guiding ridge 65 can extend over the entire ranges of arc expansions on circumferences of the bearing elements 5 and 6, respectively. In an exemplary embodiment, the guiding track 57 can be terminated at a dorsal end run 58. The dorsal end run 58 allows the prosthetic device to cease its rotation when the dorsal end facet 66 of the guiding ridge 65 comes into contact with the dorsal end run 58. As a result, the dorsal end run 58 can terminate undesired hyperextension of a joint, such as the swan-neck type of deformity from muscular disorder. In an exemplary embodiment, the dorsal end run 58 can be in hemispherical shape to accommodate hemispherical end facet 66, such as shown in FIG. 4*a*. It will be appreciated that various other embodiments of the guiding track 57 and the guiding ridge 65 are also within the scope of the present invention.

Figure 7A:
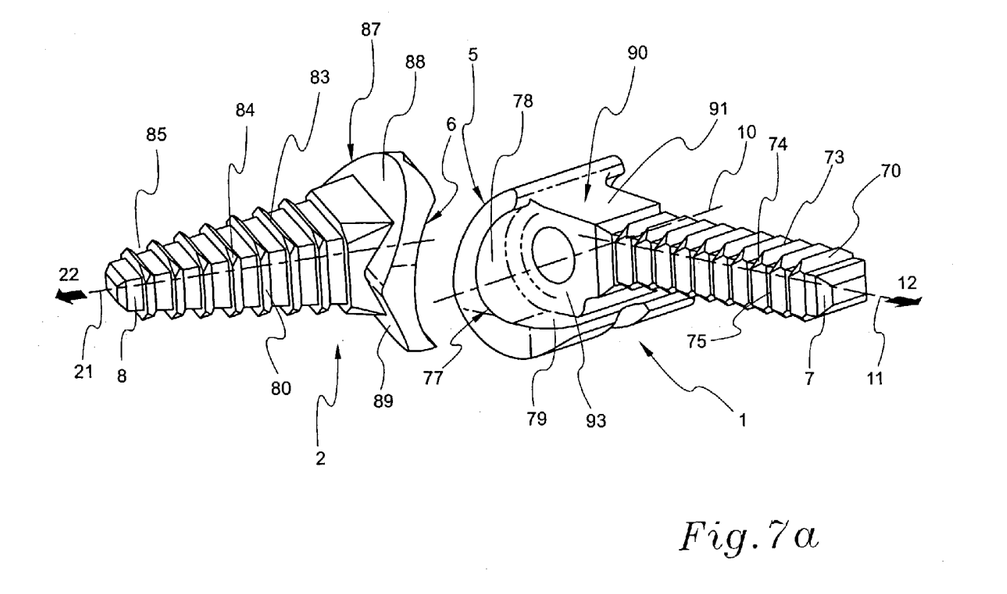
FIG. 7a is a another perspective view of the prosthetic device showing the stem elements of the first and second articular members.

The prosthetic device can be fixed to the respective bones in various manners. In one exemplary embodiment, such as shown in FIGS. 6 and 7*a*, the stem elements 7 and 8 can be provided to mount the articular members 1 and 2 onto the respective bones 3 and 4. For example, the fixation can be carried out through intramedullary anchoring which transmits substantial joint load directly onto the neck and endosteum of a transected bone shaft. The stem elements 7 and 8 can have an axial length to provide sufficient anchoring function. Additionally or alternatively, the stem elements 7 and 8 can have various cross sections. For example, the stem elements 7 and 8 can have a substantially rectangular or other multiangular shapes in the cross section to resist axial rotational moment. In an exemplary embodiment, the first stem element 7 can be adapted to maintain a substantial constant cross section along the first stem axis 11. In another exemplary embodiment, the first stem element 7 can comprise a short tapered edge in conjunction with the volar hook 92. In a further exemplary embodiment, the second stem element 8 can have a substantially constant converging cross section in the direction of distal insertion 22.

In one embodiment, the stem elements 7 and 8 can comprise a plurality of first and second flanges 70 and 80, respectively, extending circumferentially from the stem elements 7 and 8. The flanges 70 and 80 can be adapted to accommodate varying shapes of the bone shaft for initial implant fixation. For example, the first flanges 70 can be uniformly spaced from one another along the first stem element 7, such as shown in FIG. 6. In one exemplary embodiment, the first flanges 70 can be formed by a first circumferential distal surface 71 and a first proximal circumferential surface 72. In an exemplary embodiment, the first flanges 70 can have a triangular shape in an axial cross section taken along the first stem axis 11. In one exemplary embodiment, the first circumferential distal surface 71 and the first circumferential proximal surface 72 can form an acute angle therebetween, such as for stably catching onto endosteum of the intramedullary cavity. In an exemplary embodiment, the first distal surface 71 and the first proximal surface 72 can form an acute angle of about 45 degrees therebetween. In another exemplary embodiment, the second flanges 80 on the second stem element 8 can have a cross sectional shape formed similarly to that of the first flanges 70 as described above.

In one exemplary embodiment, the first and second flanges 70 and 80 can be orientated differently to accommodate different loading conditions to the bone-implant interface. For example, a joint load imposed onto the base of the bone 4 can be mainly compressive while the head of proximal 3 can receive both axial compression and bending depending on the flexion angle of the joint. In an exemplary embodiment, such as shown in FIG. 6, the first distal surface 71 can be formed to be substantially perpendicular to the stem axis 11, while the first proximal surface 72 can be about 45 degrees in relation to the stem axis 11. The first flanges 70 so formed are capable of preventing pistoning effect from varying states of joint load at different flexion angle. In another exemplary embodiment, such as shown in FIG. 6, the second proximal surface 81 can be formed to be about 45 degrees in relation to the stem axis 21, while the second distal surface 82 can be substantially perpendicular to the stem axis 21. The second flanges 80 so formed are capable of reducing shearing faces and resist subsidence of implant in long-term usage.

In another exemplary embodiment, the flanges 70 and 80 can have a multiangular circumferential shape, when being viewed in the respective directions of insertion 12 and 22. In an exemplary embodiment, one or more flanges 70 can comprise a rectangular circumferential shape formed with four sharp edges 73. In another exemplary embodiment, rectangular flanges 70 can comprise four diagonal cut-outs 74 formed at the four corners to thereby resulting in an octagonal circumferential shape, such as shown in FIG. 7*a*. In one exemplary embodiment, the diagonal cut-outs can form triangular plateaus 74, which are capable of dispersing contact stresses. In another exemplary embodiment, the second flanges 80 on the second stem element 8 can have a circumferential shape similarly to that of the first flanges 70 as described above.

In a further exemplary embodiment, one or more first recessed portions 75 can be formed between the plural flanges 70 along the stem element 7. The recessed portions 75 can be adapted to receive bone remodeling materials, such as bone graft and/or bone cement, as well as bone ingrowth from the endosteum inside a bone shaft. Thus, partial joint load can be evenly distributed throughout the enclosed cortex along the bone shaft by each segment of interlocked bone ingrowth, which is capable of providing adequate support and adhesion for a stable implant fixation. In another exemplary embodiment, similar recessed portions 85 can be formed between the second flanges 80 on the second stem element 8 similarly to that of the first recessed portions 75 as described above.

The stem elements 7 and 8 can thus fix the articular members 1 and 2 to the respective bones 3 and 4 in various manners. In an exemplary embodiment, an intramedullary anchoring can be provided by press-fitting the stem elements 7 and 8 with their respective flanges 70 and 80 into diaphyseal bone shaft for initial implant fixation immediately after surgery. Subsequent to post-operative healing, the secondary implant fixation can be achieved by macro-interlocking the bone ingrowth with the recessed portions 75 and 85 formed on the stem elements 7 and 8, respectively. It will be appreciated that various other embodiments of the stem elements 7 and 8 are also within the scope of the present invention.

Figure 7B:
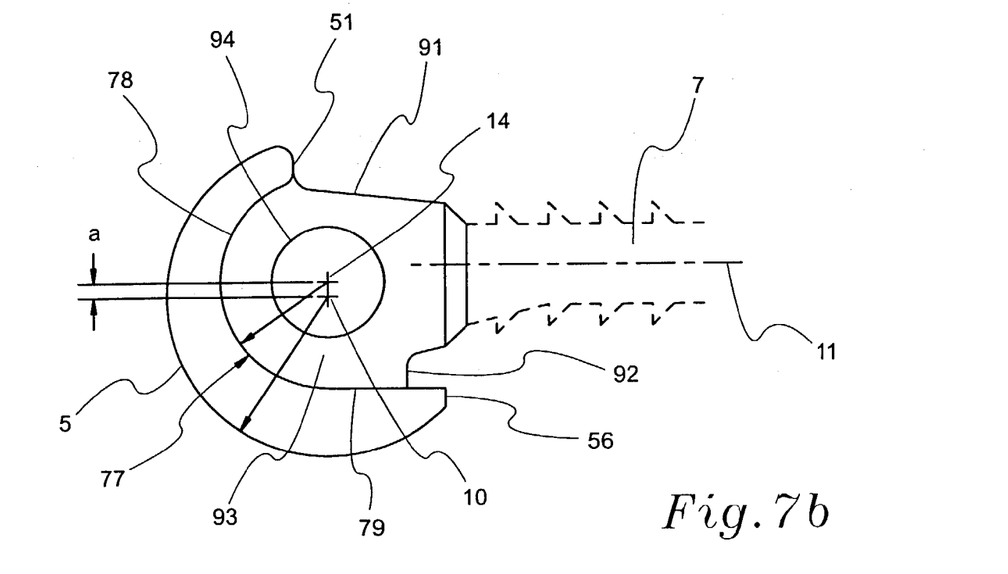
FIGS. 7b and 7c are side views of the two articular members showing their backing systems, respectively.
Figure 7C:
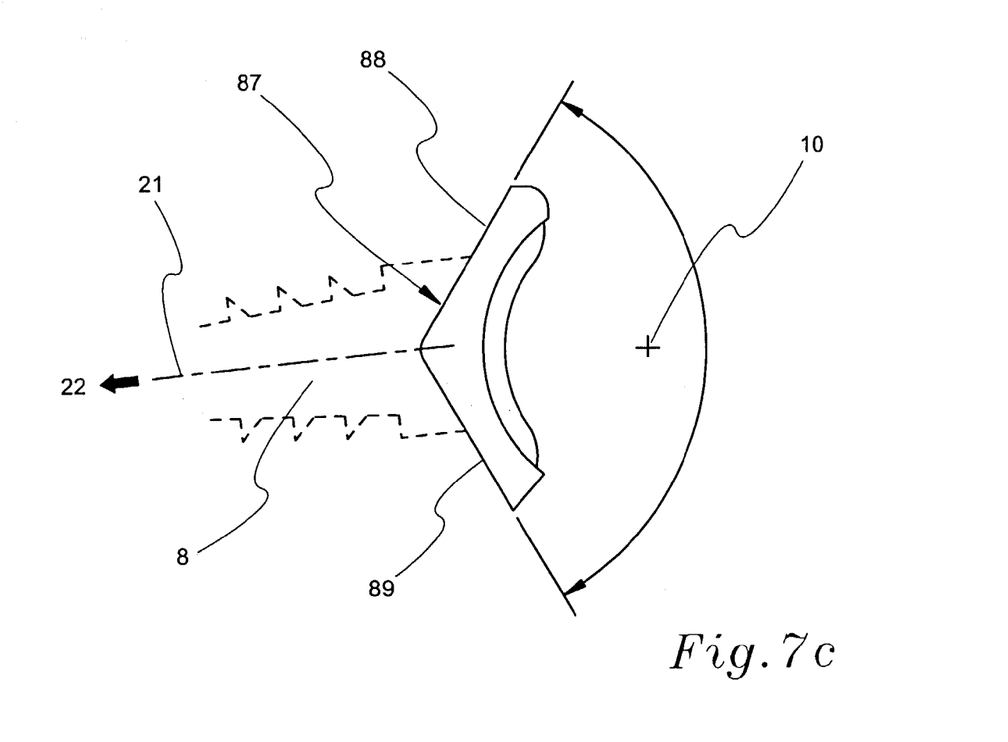

Additionally or alternatively, the articular members 1 and 2 can be mounted onto the respective bones 3 and 4 through a direct cortical support from firm seating of each bearing element 5 or 6 onto their respective well preserved bony bed for effective load transfer. In an embodiment, such as shown in FIGS. 7*a* to 7*c*, the articular members 1 and 2 can comprise backing system 77 and 87, respectively. The backing systems 77 and 87 can be formed to match their respective bone ends 34 and 44 (see FIG. 8), such as prepared according to the method of osteotomy as will be described below. The backing systems 77 and 87 can allow the minimum resection of the respective bone ends for direct load transfer between the bone ends. Additionally or alternative, the backing systems 77 and 87 are capable of preserving various soft tissue mechanisms around the implanted site to thereby maintain an anatomical structure and functional stability.

In one exemplary embodiment, such as shown in FIGS. 7a and 7b, a first backing system 77 can be formed on the first bearing element 5 opposite from the first bearing surface 50. In an exemplary embodiment, the first backing system 77 can comprise a concave cylindrical backing facet 78 and a tangential backing facet 79. In another exemplary embodiment, the concave cylindrical backing facet 78 can start at the dorsal edge 51 and extend palmarly around a backing arc axis 14 to join the tangential backing facet 79. In an exemplary embodiment, the tangential backing facet 79 can extend substantially parallel to the first stem axis 11 and the backing arc axis 14. In another exemplary embodiment, the tangential backing facet 79 can merge with the volar edge 56, such as shown in FIG. 7b. It will be appreciated that various other embodiments of the first backing system 77 are also within the scope of the present invention.

In another exemplary embodiment, such as shown in FIGS. 7a and 7c, a second backing system 87 can be formed on the second bearing element 6 opposite from the second bearing surface 60. In an exemplary embodiment, the second backing system 87 can comprise two bevel surfaces, such as the dorsal backing facet 88 and the volar backing facet 89. In another exemplary embodiment, the two bevel surfaces 88 and 89 can provide a wedge-like structure with an obtuse angle, such as of about 120 degrees, pointing in the direction of distal insertion 22. When the second articular member 2 is subject to a compressive joint load, the second backing system 87 is capable of being firmly seated onto the resected valley of the bone end 44 (see FIG. 8). Thus, the second backing system 87 is capable of increasing the effective surface contact area during a direct bone-implant load transfer. Additionally or alternatively, the wedge-like second backing system 87 is capable of providing the second bearing element 6 with resistance to rotation along the second stem axis 21. It will be appreciated that various other embodiments of the second backing system 87 are also within the scope of the present invention.

In another embodiment, such as shown in FIGS. 7a and 7b, an intermediate base 90 can be provided and connected between the first bearing element 5 and the first stem element 7. The intermediate base 90 can be custom configured to be seated into, such as the bony metaphyseal site. For example, the intermediate base 90 can be in direct contact with the first backing system 77. Additionally or alternatively, the intermediate base 90 can extend to merge with the first fixation stem 7. In an exemplary embodiment, the intermediate base 90 can have a dorsal facet 91 slightly slope down from the dorsal edge 51, such as to accommodate the slight converging head of the bone 3. In another exemplary embodiment, a cut-out portion can be provided on the intermediate base 90 adjacent to the volar edge 56 forming a volar hook 92, such as for interlocking onto the palmar cortex of a resected bone end. In a further exemplary embodiment, the intermediate base 90 can comprise a pair of laterally indented facets 93 for accommodating the preserved bone stock for direct load transfer. In one exemplary embodiment, an axial cross section of the first articular member 1 can be substantially T-shaped, such as shown in FIG. 6.

In another exemplary embodiment, a lateral aperture 94 can be provided in the intermediate base 90 to pass through both lateral facets 93 along the backing arc axis 14. The lateral aperture 94 can be provided to enhance fixation by interlocking the intermediate base 93 with the bone ingrowth, bone allograft, and/or bone cement. For example, the lateral aperture 94, after implantation, can be located right between the origins of the collaterial ligaments at the head of the bone 3, such as to facilitate surgical reconstruction of the collaterial ligament. In an exemplary embodiment, the backing arc axis 14 can be offset from the joint rotational axis 10 by a dorsal offset "a", such as shown in FIG. 7b. The dorsal offset "a" can allow the thickness of the first bearing element 5 to increase and reach a maximum thickness at the palmar region. Such increased thickness of the bearing element 5 can effectively provide additional strength to the bearing element 5 to counter a higher joint load arising from any power gripping hand function. It will be appreciated that various other embodiments of the intermediate base 90 are also within the scope of the present invention.

Various materials can be used to form the articular members 1 and 2 of the prosthetic device. For example, the prosthetic device can be formed of a material capable of providing a high durability to withstand repeated stresses from normal body activities and/or a high abrasive resistance to minimize wear and tear damages to the implanted bearing elements 5 and 6. In an exemplary embodiment, the prosthetic device can be made of a metal to provide sufficient strength and prolonged usage over the lifespan of patient. In another exemplary embodiment, the prosthetic device can be made of high performance metallic cobalt chromium (CoCr) alloy. The clinically proven biocompatibility of such material enables all features of the present invention to be performed effectively with little hostile effect under salinity of body fluid and body temperature.

According to another aspect, a resection method can be provided to prepare a defective articulation for receiving the prosthetic device. For example, the resection method can comprise removing the defective articulation and preparing the remaining bone ends to closely resemble the natural articular cartilage. In one embodiment, the resection of the defective articulating surface can be carried out closely along the boundary of the articular cartilage where sufficient bone stock can be available for direct load transfer. In an exemplary embodiment, the resection can be carried out at a defective articulating surface where the remaining tendon and ligamentous attachments are well preserved to maintain an original anatomical structure of a natural joint. In another exemplary embodiment, the method can comprise minimizing resection of the bone ends to carry out direct load transfer between the bone ends. In a further exemplary embodiment, the method can comprising preserving various soft tissue mechanisms around the implanted site to maintain an anatomical structure and functional stability.

Figure 8:
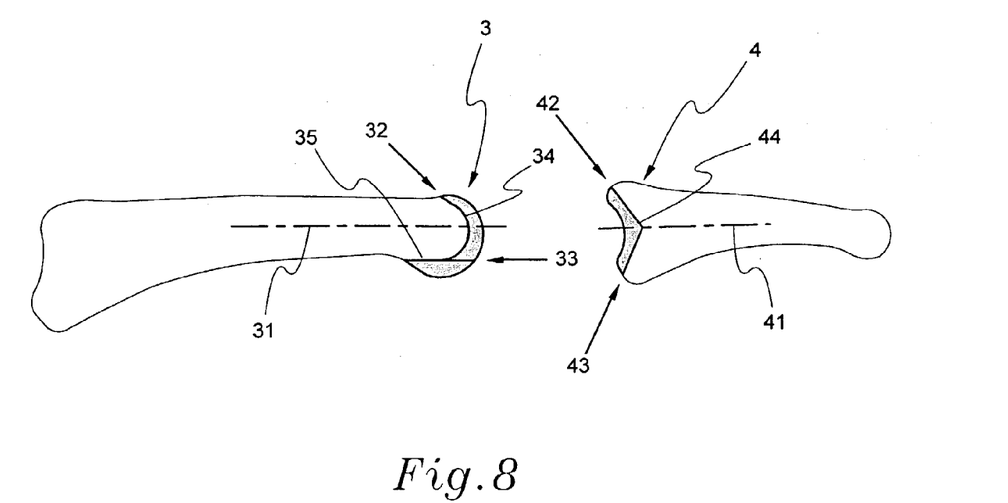
FIG. 8 shows two bones having proposed resections to bone ends at the joint according to the resection method.

While the resection method can be performed to various bone ends, such as shown in FIG. 8, an exemplary resection method is now described in connection with the resection to the head of the bone 3, such as a proximal phalanx, to prepare a bone end 34. In one exemplary embodiment, the resection method can comprise preparing bone end 34 to closely conform to the head of the bone 3. In an exemplary embodiment, a circumferential cut 32 can be carried out palmarly to remove the defective articular cartilage at the head of the bone 3. In another exemplary embodiment, a straight cut 33 can be carried out volarly along the longitudinal bone axis 31 to remove the defective articular cartilage and bypass the origins of the collaterial ligaments 36 accordingly. In a further exemplary embodiment, the resection method can comprise preparing the bone 3 to receive a fixation element, such as the first stem element 7. For example, the resection method can comprise reaming the shaft of bane 3 along the longitudinal bone axis 31. In a still further exemplary embodiment, the resection method can comprise preparing the bone 3 to provide additional rotational stability to the bone-implant interface. For example, two shoulders (not shown) can be prepared in the reamed bone shaft (or matching the indented facets 93 of articular member 1. A volar notch 35 can be formed on the head of the bone 3.

In another exemplary embodiment, the resection method is shown to be carried out to the base of the bone 4, such as a middle phalanx, to prepare a bone end 44. In one exemplary embodiment, the resection method can comprise preparing bone end 44 to closely conform to the base of the bone 4. In an exemplary embodiment, two bevel cuts 42 and 43 are carried out dorsopalmarly to the base of the bone 4 up to the longitudinal bone axis 41. In another exemplary embodiment, a bone end valley 44 can be formed for receiving the wedge-like second backing system 87 of the second articular member 2, such as to retain both the central attachment of the extensor central tendon 45 and the palmar margin of the volar plate 46. In a further exemplary embodiment, the resection method can comprise reaming the shaft of bone 4 along the longitudinal bone axis 41, such as for receiving the second stem element 8. It will be appreciated that various other embodiments of preparing the bone ends are also within the scope of the present invention.

Figure 9:
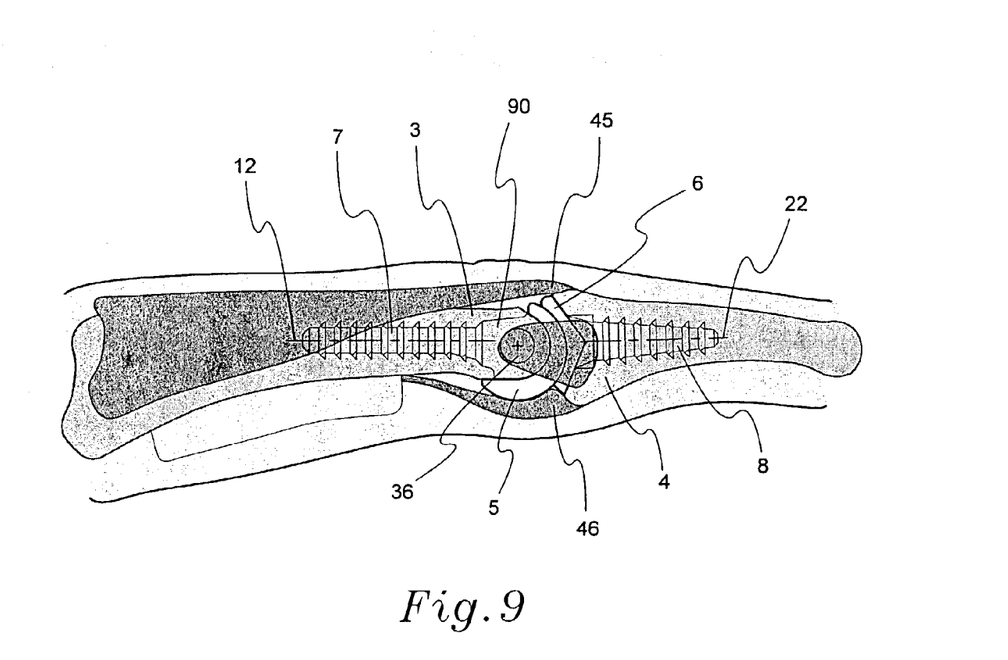
FIG. 9 is a partial side sectional view showing the preserved soft tissue arrangement surrounding the prosthetic device after being implanted in the adjoining bones to replace a joint.

As exemplified in FIG. 9, the prosthetic device and/or the resection method are capable of preserving the various original tendons and ligamentous arrangement for maintaining the joint stability after the surgery. Additionally or alternatively, the prosthetic device and/or the resection method can allow surgical reconstruction to the soft tissue mechanisms to be carried out without interference from the prosthetic device implanted between the bones 3 and 4. For example, surgical intervention for collateral ligament reconstruction and/or tendon grafting can be carried out.

Figure 10:
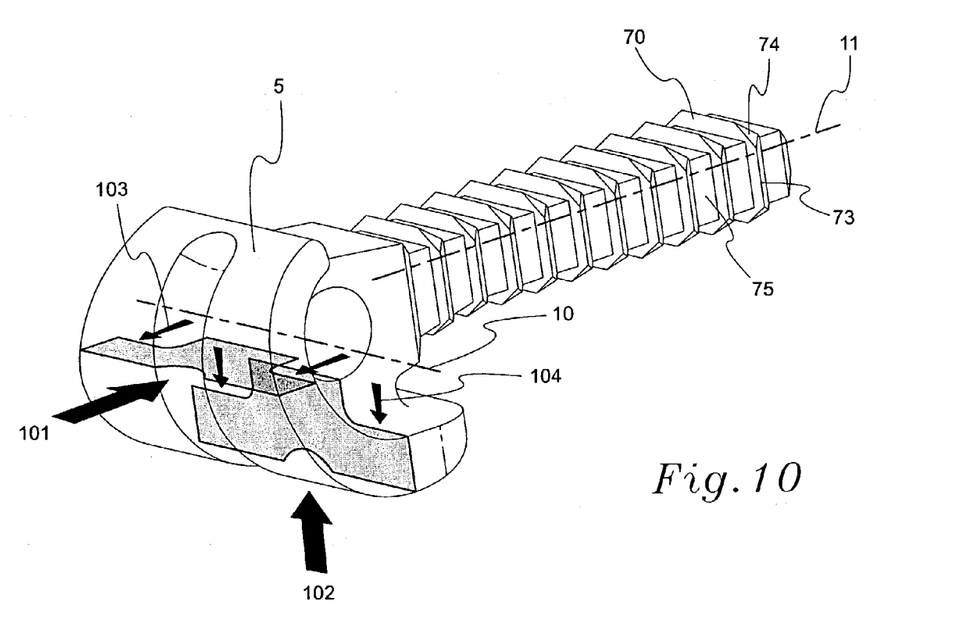
FIG. 10 illustrates the load transmission in the first articular member at the junction between the first backing system and the corresponding bone end.

Additionally or alternatively, the prosthetic device and/or the resection method can allow joint load to be transferred perpendicularly at the bone-implant interface to provide adequate bony support even at different joint flexion angle. For example, the bone-implant interface can be provided by the closely conformed resected bone ends 34 and 44 and the respective backing systems 77 and 87. FIG. 10 illustrates the load transfer in the first articular member 1. For example, the joint load at extension 101 and flexion 102 exerted on the bearing element 5 can be in a compressive form and resisted perpendicularly by the bony support 103 and 104, such as provided by the resected bone ends 34 and 44. Thus, the prosthetic device and/or the resection method are capable of avoiding triggering of any shearing component to the bone-implant interface, which can be hazardous leading to implant dislocation.

It will be appreciated that the various features described herein can be used solely or in any combination thereof. Therefore, the present invention is not limited to only the embodiments specifically described herein. While the foregoing description and drawings represent a preferred embodiment of the present invention, it will be understood that various additions, modifications, and substitutions can be made therein without departing from the spirit and scope of the present invention as defined in the accompanying claims. The presently disclosed embodiment is therefore to be considered in all respects as illustrative and not restrictive, the scope of the invention being indicated by the appended claims, and not limited to the foregoing description.

What is claimed is:

1. A prosthetic device for replacing a joint, comprising a first articular member and a second articular member to be mounted onto adjoining bones,
   wherein the first articular member comprises:
      a first bearing element comprising a first convex bearing surface;
      a first contoured backing system formed on the first bearing element for anchoring towards a first bone end; and
      a first stem element for mounting the first articular member to a first bone;
   wherein the second articular member comprises:
      a second bearing element comprising a second concave bearing surface;
      a second contoured backing system formed on the second bearing element for anchoring towards a second bone end and having a wedge shape; and
      a second stem element for mounting the second articular member to a second bone; and
   wherein the second bearing element is adapted to rotate around the first bearing element while the second bearing surface slides along the first bearing surface.

2. The prosthetic device of claim 1, wherein the first bearing surface comprises a trapezoidal boundary.

3. The prosthetic device of claim 2, wherein the first convex bearing surface comprises a dorsal edge and a volar edge, the dorsal edge and the volar edge defining a first arc expansion of the first convex bearing surface to allow the articular members to fully flex as a natural joint.

4. The prosthetic device of claim 3, wherein the first convex bearing surface comprises a pair of lateral taper edges extending between the dorsal edge and the volar edge and forming a trapezoidal shape to provide an increasing contact area towards the region of joint flexion.

5. The prosthetic device of claim 3, wherein the first arc expansion is displaced angularly and palmarly along a first joint rotational axis.

6. The prosthetic device of claim 3, wherein the first arc expansion is about 30 degrees displaced angularly and palmarly along a joint rotational axis.

7. The prosthetic device of claim 1, wherein the second concave bearing surface comprises an elliptical boundary.

8. The prosthetic device of claim 7, wherein the second concave bearing element comprises a dorsal protruding lip extending at the end boundary of the dorsal arc portion for restraining joint subluxation.

9. The prosthetic device of claim 7, wherein the second concave bearing element comprises a volar recessed facet to accommodate natural arrangements of extensor tendon and volar plate.

10. The prosthetic device of claim 2, wherein the second concave bearing surface defines a second arc expansion between the dorsal protruding lip and the volar recessed facet.

11. The prosthetic device of claim 1, wherein the bearing surfaces are cylindrical.

12. The prosthetic device of claim 1, wherein the bearing elements comprise complementary guiding elements to provide joint alignment and lateral constraint.

13. The prosthetic device of claim 12, wherein:
   the first bearing element comprises a guiding track extending circumferentially on the first convex bearing surface; and the second bearing element comprises a guiding ridge extending circumferentially on the second concave bearing surface, the guiding ridge being slideably received in the guiding track to provide joint alignment and lateral constraint.

14. The prosthetic device of claim 13, wherein the guiding track is terminated at a dorsal end run to provide constrain at the articulation of the articular members.

15. The prosthetic device of claim 1, wherein the first backing system is located opposite from the first convex bearing surface, the first backing system comprising:
a concave cylindrical backing facet extending from a dorsal edge formed on the first convex bearing surface; and
a tangential backing facet extending continuously from the concave cylindrical backing facet to a volar edge formed on the first convex bearing surface, the tangential backing facet being substantially parallel to a stem axis;
wherein the concave cylindrical backing facet smoothly merges with the tangential backing facet.

16. The prosthetic device of claim 15, wherein the curvature radius of the concave cylindrical backing facet is smaller than that of the first convex bearing surface which essentially defines the basic thickness of the first bearing element.

17. The prosthetic device of claim 15, wherein the central axis of the concave cylindrical backing facet is dorsally offset from the joint rotational axis to provide an increasing thickness to the first bearing element palmarly.

18. The prosthetic device of claim 1, wherein the first articular member further comprises an intermediate base, which merges with the first backing system and joins to the first stem element.

19. The prosthetic device of claim 18, wherein the intermediate base comprises a dorsal facet which slopes down from a dorsal edge of the first bearing element.

20. The prosthetic device of claim 18, wherein the intermediate base comprises a pair of laterally indented facets so that the intermediate base forms a T-shape in an axial cross section of the first articular member.

21. The prosthetic device of claim 18, wherein the intermediate base defines a lateral through aperture therein.

22. The prosthetic device of claim 18, wherein the intermediate base comprises a volar hook to prevent dorsopalmar displacement of the first articular member upon implantation.

23. The prosthetic device of claim 1, wherein the second backing system is located opposite from the second bearing surface and comprises two bevel surfaces.

24. The prosthetic device of claim 1, wherein each stem element comprises a rectangular cross-section to prevent axial rotation.

25. The prosthetic device of claim 1, wherein each stem element comprises a plurality of flanges located along the stem axis, each pair of adjacent flanges defining a recessed portion therebetween far bone-ingrowth.

26. The prosthetic device of claim 25, wherein each flange comprises a circumferential proximal surface and a circumferential distal surface forming an acute angle therebetween.

27. The prosthetic device of claim 26, wherein one of the circumferential proximal surface and the circumferential distal surface forms about 45 degrees in relation to the stem axis.

28. The prosthetic device of claim 27, wherein one or more of the circumferential proximal surfaces in the first stem element form about 45 degrees in relation to a first stem axis.

29. The prosthetic device of claim 27, wherein one or more of the circumferential proximal surfaces in the second stem element form about 45 degrees in relation to a second stem axis.

30. The prosthetic device of claim 25, wherein each flange comprises a substantially rectangular circumference.

31. The prosthetic device of claim 26, wherein each flange comprises four sharp edges formed by the intersected circumferential distal and proximal surfaces and four diagonal triangular plateaus.

32. A prosthetic device for replacing a joint, comprising a first articular member and a second articular member to be mounted onto adjoining bones,
wherein the first articular member comprises:
a first bearing element comprising a first convex bearing surface;
a first contoured backing system formed on the first bearing element for anchoring towards a first bone end; and
a first stem element for mounting the first articular member to a first bone;
wherein the second articular member comprises:
a second bearing element comprising a second concave bearing surface which comprises an elliptical boundary;
a second contoured backing system formed on the second bearing element for anchoring towards a second bone end; and
a second stem element for mounting the second articular member to a second bone; and
wherein the second bearing element is adapted to rotate around the first bearing element while the second bearing surface slides along the first bearing surface; and
wherein the elliptical boundary of the second concave bearing surface comprises volar and dorsal arc portions with different radii of curvature.

33. The prosthetic device of claim 32, wherein the radius of the volar arc is in a scale factor from about 2.5 to about 2.9 larger than the radius of the dorsal arc.

34. A prosthetic device for replacing an interphalangeal joint of a human finger, comprising a first articular member and a second articular member to be mounted onto adjoining phalangeal bones,
wherein the first articular member comprises:
a first bearing element comprising a first convex bearing surface, which has a frontal profile configured with a trapezoidal boundary and a palmar profile configured with a rectangular boundary acting as the joint surface of a human finger joint;
a first contoured backing system in a concave configuration formed underneath the first bearing element for proper sitting of the first bearing element onto a first bone end;
a first intermediate base in rectangular form extending from the first contoured backing system for anchoring into a first bone; and
a first stem element in octagonal section for mounting the first articular member to the compact bone of the first bone;
wherein the second articular member comprises:
a second bearing element comprising a second concave bearing surface, which has a frontal profile configured with an elliptical boundary acting as a joint surface of adjoining human joint;

a second contoured backing system in wedge configuration formed underneath the second bearing element for proper sitting the second bearing element onto a second bone end; and a second stem element in octagonal section for mounting the second articular member to the compact bone of a second bone; and wherein the second bearing element is adapted to rotate around the first bearing element while the second bearing surface slides along the first bearing surface under normal physiological joint load without any linking mechanism in between.

35. The prosthetic device of claim 34, wherein the first convex bearing surface comprises a dorsal edge and a volar edge, the dorsal edge is shorter than that of the volar edge which defines a first arc expansion of the first convex bearing surface with a constant radius to allow the articular members to fully flex as a natural joint at a fixed joint rotation axis.

36. The prosthetic device of claim 34, wherein the second concave bearing surface defines a second arc expansion between the dorsal protruding lip and the volar recessed facet with a constant radius to allow the articular members to fully flex as a natural joint at a fixed joint rotation axis.

37. The prosthetic device of claim 34, wherein the bearing surfaces are cylindrical with a constant radius of curvature.

38. The prosthetic device of claim 34, wherein the bearing elements comprise complementary guiding elements so configured in constant section of semi-circular form to provide gradual joint alignment and varied lateral constraint in response to different level of imposed joint loading without any linking mechanism, wherein:

the first bearing element comprises a guiding track extending circumferentially on the first convex bearing surface; and the second bearing element comprises a guiding ridge extending circumferentially on the second concave bearing surface, the guiding ridge being slideably received in the guiding track to provide joint alignment and lateral constraint.

39. The prosthetic device of claim 35, wherein the first backing system is located opposite from the first convex bearing surface, the first backing system comprising:

a concave cylindrical backing facet with a constant radius of curvature extending from a dorsal edge formed on the first convex bearing surface; and a tangential backing facet extending continuously from the concave cylindrical backing facet to a volar edge formed on the first convex bearing surface, the tangential tacking facet being substantially parallel to a stem axis;

wherein the concave cylindrical backing facet smoothly merges with the tangential backing facet.

40. The prosthetic device of claim 34, wherein each stem element comprises a plurality of octagonal flanges located along the stem axis, each pair of adjacent flanges defining a recessed portion with interval distance twice the thickness of the octagonal flanges therebetween for bone anchoring.

41. The prosthetic device of claim 40, wherein each flange comprises a substantially octagonal circumference.

* * * * *